United States Patent
Chayat (10) Patent No.: US 9,615,765 B2
(45) Date of Patent: Apr. 11, 2017

(54) WIDEBAND RADAR WITH HETEROGENEOUS ANTENNA ARRAYS

(75) Inventor: Naftali Chayat, Kfar Saba (IL)

(73) Assignee: VAYYAR IMAGING LTD., Yehud (IL)

( * ) Notice: Subject to any disclaimer, the term of this patent is extended or adjusted under 35 U.S.C. 154(b) by 0 days.

(21) Appl. No.: 13/602,333

(22) Filed: Sep. 4, 2012

(65) Prior Publication Data

US 2014/0066757 A1    Mar. 6, 2014

(51) Int. Cl.
| | |
|---|---|
| *G01S 13/89* | (2006.01) |
| *H01Q 21/30* | (2006.01) |
| *A61B 5/05* | (2006.01) |
| *G01S 7/40* | (2006.01) |
| *G01S 13/02* | (2006.01) |
| *H01Q 13/08* | (2006.01) |
| *H01Q 21/20* | (2006.01) |
| *H01Q 21/26* | (2006.01) |
| *H01Q 5/42* | (2015.01) |
| *H01Q 21/06* | (2006.01) |
| *G01S 7/02* | (2006.01) |
| *A61B 5/00* | (2006.01) |

(52) U.S. Cl.
CPC .......... *A61B 5/0507* (2013.01); *G01S 7/4021* (2013.01); *G01S 13/0209* (2013.01); *G01S 13/89* (2013.01); *H01Q 5/42* (2015.01); *H01Q 13/085* (2013.01); *H01Q 21/064* (2013.01); *H01Q 21/20* (2013.01); *H01Q 21/26* (2013.01); *A61B 5/4312* (2013.01); *A61B 2562/0228* (2013.01); *A61B 2562/046* (2013.01); *G01S 7/024* (2013.01); *G01S 2013/0245* (2013.01)

(58) Field of Classification Search
USPC ........................................................ 600/430
See application file for complete search history.

(56) References Cited

U.S. PATENT DOCUMENTS

| | | |
|---|---|---|
| 5,537,367 A | 7/1996 | Lockwood et al. |
| 6,130,958 A | 10/2000 | Rohler et al. |
| 2003/0137456 A1 | 7/2003 | Sreenivas et al. |
| 2004/0077943 A1 | 4/2004 | Meaney et al. |
| 2006/0183995 A1 | 8/2006 | Bond et al. |
| 2009/0135078 A1 | 5/2009 | Lindmark et al. |
| 2009/0273533 A1* | 11/2009 | Wolf et al. ................. 343/770 |
| 2010/0164784 A1 | 7/2010 | Longstaff |

(Continued)

OTHER PUBLICATIONS

Klemm et al., Microwave Radar-Based Differential Breast Cancer Imaging: Imaging in Homogeneous Breast Phantoms and Low Contrast Scenarios, IEEE Transactions on antennas and propagation, vol. 58, No. 7, Jul. 2010.*

(Continued)

*Primary Examiner* — Katherine Fernandez
*Assistant Examiner* — Farshad Negarestan
(74) *Attorney, Agent, or Firm* — Mark Cohen; Pearl Cohen Zedek Latzer Baratz (57) ABSTRACT

A heterogeneous antenna array containing antenna elements of different antenna element sizes interleaved among one another is disclosed. Heterogeneous antenna arrays as disclosed herein can efficiently cover a broad range of frequencies without loss of optimality at higher frequencies. Also disclosed are methods of frequency-domain oriented image reconstruction which are suitable for use with heterogeneous antenna arrays.

8 Claims, 5 Drawing Sheets

(56) References Cited

U.S. PATENT DOCUMENTS

2010/0289717 A1* 11/2010 Arslan et al. ................ 343/876
2011/0237939 A1    9/2011 Melamed et al.

OTHER PUBLICATIONS

International Search Report for PCT Application No. PCT/IL2013/050749 mailed Jan. 14, 2014.
Supplementary European Search Report for European Application No. 13834968.3 dated Mar. 23, 2016.

* cited by examiner

WIDEBAND RADAR WITH HETEROGENEOUS ANTENNA ARRAYS

BACKGROUND

Radar arrays are typically designed and/or optimized for a specific wavelength range. Arrays are typically composed of identical antenna elements arranged in a regular pattern, such as rectangle. Antenna element spacing is typically chosen to be on the order of half-wavelength at the operating frequency. This permits a large angular scanning range and avoids grating lobes, which occur in spurious directions where the received signals are out of phase by a non-zero integral number of wavelengths.

Certain new radar applications, however, benefit from wideband signals for which traditional arrays are not optimal. With wideband radar it is impossible to satisfy the half wavelength condition for all frequencies in the band, since the spacing between elements may be on the order of half-wavelength at the lowest operating frequency of the array, but is one wavelength at twice the lowest frequency, two wavelengths at four-times the lowest frequency, and so forth. As a result, at higher frequencies there is a directional ambiguity, or in case of near-field microwave imaging (such as in medical applications) an under-utilization of the spatial resolution achievable at the different frequencies.

The design of wideband antenna arrays thus poses several difficulties. One difficulty involves designing small wideband antenna elements having a minimum gain in all frequencies of interest. Another difficulty relates to antenna element size. Antenna element and array sizes are dictated by the lower edge of the band covered. As a result, the array density is sub-optimal for the upper edge of the band.

Among the new applications which can benefit from wideband radar are medical imaging techniques for mapping the interior of the human body and detecting anomalies such as malignant tumors, particularly in breast tissue. Microwave imaging of the human breast has been of interest, both in view of its medical and social importance, and in view of the relatively low-loss materials of the breast.

Signals used for scanning the human body typically occupy frequencies from about 10 MHz to 10 Ghz. Particular attention has recently been drawn to the 3.1 to 10.6 GHz range, which allows license-exempt ultra-wideband (UWB) operation at low signal levels. There is an advantage to using lower frequencies in view of better penetration into the human body, but higher frequencies are desirable in view of their shorter wavelength and better spatial resolution. Use of wideband radar allows high temporal resolution, facilitating discrimination of features according to their depth (distance from the antenna array). The maximum frequency of the signal determines the image resolution, but using only high frequencies is not adequate, due to their low penetration and on account of the appearance of artifacts related to phase ambiguity. It is thus beneficial to use a wide range of frequencies.

Other restrictions on microwave imaging include the need to penetrate the outer attenuating layers of the human body in order to identify underlying features. The faint variations in signal reflection from underlying features are typically masked by reflections from the antenna elements themselves and the tails of reflections from closer features, such as the interface with the skin. Current techniques for overcoming these problems include: calibrating the antenna arrays; cancelling out the contribution of surface layers so as not to interfere with detecting the interior features; and algorithms for reconstructing the spatial map of dielectric properties of the object from multi-antenna element observations. Current algorithms include basic "delay-and-sum" (DAS) algorithms, as well as more intricate inverse-problem algorithms. Nevertheless, current methods still suffer from residual errors and limited dynamic range.

One of the shortcomings of basic DAS algorithms, as well as other current reconstruction algorithms, is that they assume antenna elements to be perfectly isotropic, and that signal paths are lossless. In practice, however, antenna elements have direction-dependent radiation patterns as well as frequency-dependent gains and phase shifts. Practical implementations of current reconstruction algorithms, therefore seek to cancel out these effects by a pre-processing stage that is separate from the reconstruction algorithm itself, e.g., by calibrating the antenna elements and dividing or de-convolving the measured signals by reference calibration signals containing the antenna element gain and phase shift. However, separating the calibration from the image reconstruction is sub-optimal and increases noise and artifacts. For example, if one of the antenna elements receives the target object reflection faintly due to a null in its radiation pattern, pre-calibration techniques merely compensate by over-amplifying the weak signal (along with its noise and artifacts), whereas the appropriate response is to simply ignore the signals from this antenna element.

An additional problem arises on account of path loss caused by propagation in space as well as signal attenuation in the target medium, where the signals arriving from an arbitrary point in the medium to the antenna array arrive at different gains. As noted previously, if this gain is cancelled out before applying the DAS algorithm, then noise amplification may result. Other sources of gain and phase variations in the system include its electrical components (transceivers, mixers, cables, etc).

Another type of phase variation is created by frequency variation in the relative electrical permittivity ($\in_r$) of the medium. This leads to dispersion, where different frequencies have different propagation velocities in the medium.

In general, various frequency-dependent effects contribute to variability in signal amplitude and phase shift according to frequency. In addition, some of these effects (such as antenna array and element radiation pattern, frequency dependence of $\in_r$) affect amplitude and phase shift according to target object location and signal path, and therefore cannot be cancelled separately.

SUMMARY

Embodiments of the present invention provide wideband "heterogeneous arrays" that overcome the above-noted difficulties and restrictions. Heterogeneous arrays according to embodiments of the invention are composed of different sub-arrays interspersed with one another. The different sub-arrays are designed and optimized for different frequencies and/or frequency ranges. Embodiments of the invention thereby alleviate the requirement to design a single antenna array or element covering a large bandwidth. In addition, some embodiments provide sub-arrays that are sparser for the lower frequencies and denser for the higher frequencies, allowing an increased density of the array that is not limited by the lowest frequency. In certain embodiments, the sub-arrays use different antenna element types, with potentially different spatial and frequency characteristics. Some embodiments employ antenna elements having different polarizations, in order to collect additional data about the target object.

For purposes of illustration, principles of the present invention are discussed herein in terms of microwave antenna arrays, such as radar and near-field medical diagnostic imaging. It is understood, however, that these examples and embodiments are non-limiting. Embodiments of the present invention cover a variety of applications, including, but not limited to: radar in general; commercial and industrial imaging; microwave hyperthermia therapy; and examination and testing based on transmission and/or attenuation.

For heterogeneous arrays, the different sub-arrays provide different densities and different gains for different frequencies and/or frequency ranges. Therefore, signals received by different sub-arrays do not contain the same information, and thus simply applying the standard DAS algorithm does not yield an optimal reconstructed image. Accordingly, embodiments of the invention provide frequency domain reconstruction techniques to overcome this restriction, as well as other problems related to gain and phase variations. For optimal results, embodiments of the invention factor these effects holistically into the image reconstruction, rather than treat them as extraneous variables for compensation prior to reconstruction, as is typically done in the prior art.

To correctly resolve amplitude and phase-shift frequency-dependencies discussed previously, certain embodiments of the invention provide image reconstruction methods based on Minimum Mean Square Error (MMSE), to optimally weight the signals from different antenna arrays/sub-arrays based on frequency response.

Certain embodiments of the present invention provide improved MIMO based microwave imaging which offers advantages in detecting malignant tumors in a human body, and, in particular, in breast tissue.

BRIEF DESCRIPTION OF THE DRAWINGS

The subject matter disclosed may best be understood by reference to the following detailed description when read with the accompanying drawings in which.

For simplicity and clarity of illustration, elements shown in the figures are not necessarily drawn to scale, and the dimensions of some elements may be exaggerated relative to other elements. In addition, reference numerals may be repeated among the figures to indicate corresponding or analogous elements.

DETAILED DESCRIPTION

In the present disclosure, embodiments of the invention are illustrated in terms of a non-limiting example of near-field medical diagnostic imaging, it being understood that the invention is not limited to this particular area and that embodiments of the invention are also applicable to other areas of the radar and microwave signal field.

Heterogeneous Arrays

According to certain embodiments of the invention, different antenna element sizes are interleaved within an antenna array as antenna sub-arrays for handling different respective frequency subranges. In a specific embodiment, the lowest octave of frequencies are covered by antenna elements tuned to that range, at element spacing which is 0.5 to 1 wavelength for this particular frequency range. For the second octave, a different sub-array is used, with half the size for each antenna element and twice the linear density (4 times per unit area) of elements. As a result, in the second octave of frequencies, the spacing between the elements is again 0.5 to 1 wavelength. In related embodiments, this process is continued for a third octave and so on. The interleaving of the arrays on the same surface can take different forms, for example with microstrip patch antenna elements smaller antenna elements can be placed above the larger antenna elements so that the larger antenna elements serve as a ground plane for the lower frequency antenna elements. In another embodiment, UWB antenna elements covering the whole range of operating frequencies will form the initial array. These antenna elements can be supplemented by additional, smaller antenna elements filling the gaps between the original antenna elements so that at higher frequency the additional antenna elements in conjunction with the original antenna elements form a denser array.

According to embodiments of the invention, an antenna sub-array contains one or more antenna elements which are congruent with one another. Two antenna elements are congruent if they have the same shape and the same physical dimensions in all directions (in a non-limiting example of Cartesian coordinates: length, width, and height). According to further embodiments of the invention, two antenna elements are transformal with respect to one another in one given physical dimension, if they have the same shape, but differ in physical extent in that physical dimension. According to certain embodiments of the invention as discussed below, an antenna element of one sub-array may be transformal in at least one physical dimension with respect to an antenna element of a different sub-array, but only within the same sub-array are the antenna elements congruent. In these embodiments, an antenna element of one sub-array is transformal, but not congruent, to an antenna element of another sub-array. According to other embodiments of the invention, an antenna element of one sub-array is neither congruent nor transformal to an antenna element of another sub-array.

In embodiments of the invention, "antenna element size" refers to the wavelength (or frequency) and/or wavelength range (or frequency range) of the electromagnetic spectrum which an antenna element has been designated and/or optimized to handle. If a first antenna element is described as being of a different size from that of a second antenna element, it means that the first antenna element operates at a different wavelength and/or wavelength range from that of the second antenna element. In embodiments of the invention, this is equivalent to describing the first antenna element as operating at a different frequency and/or frequency range from that of the second antenna element. It is noted that, with regard to embodiments of the invention, the term "antenna element size" is not necessarily the same as a "physical dimension", as used above to relate to congruence and transformality.

According to certain embodiments of the invention, interleaving different antenna element sizes means that at least one antenna element of a first antenna element size is surrounded by two or more antenna elements of a second antenna element size. In additional embodiments of the invention, the majority of antenna elements of the first antenna element size are surrounded by two or more antenna elements of the second antenna element size. In some embodiments of the invention, the antenna elements are arranged in a single direction ("one-dimensional array"). In other embodiments of the invention, the antenna elements are arranged in two different directions ("two-dimensional array"). The term "surrounded by" herein denotes that an antenna element of one sub-array is positioned immediately between or among antenna elements of one or more different antenna sub-arrays.

In embodiments of the present invention, shorter wavelength sub-arrays are interleaved within longer wavelength sub-arrays, such that a shorter wavelength antenna element is surrounded by (positioned immediately between) longer wavelength antenna elements. In related embodiments, the interleaving is such that a longer wavelength antenna element is surrounded by shorter wavelength antenna elements. In another embodiment, there is at least one antenna sub-array that has an antenna element which is surrounded by antenna elements of a different antenna sub-array. In still other embodiments, every antenna sub-array has at least one antenna element that is surrounded by antenna elements of a different antenna sub-array.

In certain embodiments of the invention, a frequency and/or frequency range can overlap different (heterogeneous) sub-arrays. In these embodiments, therefore, the antenna element characteristics for that specific frequency and/or frequency range (including, but not limited to density and gain) are a function of the combined properties of all the overlapping sub-arrays.

Figure 1A:
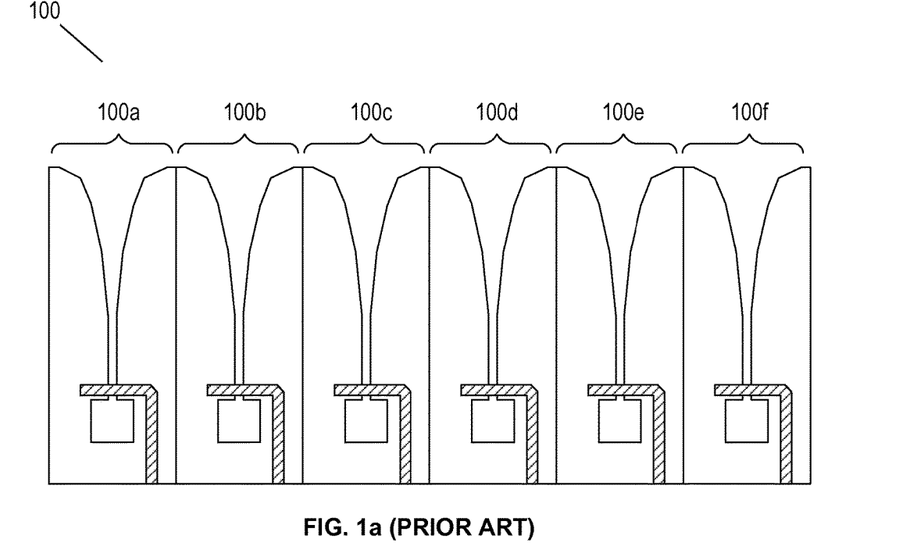
FIG. 1a illustrates a layout of an exemplary one-dimensional homogeneous antenna array according to the prior art.
Figure 1B:
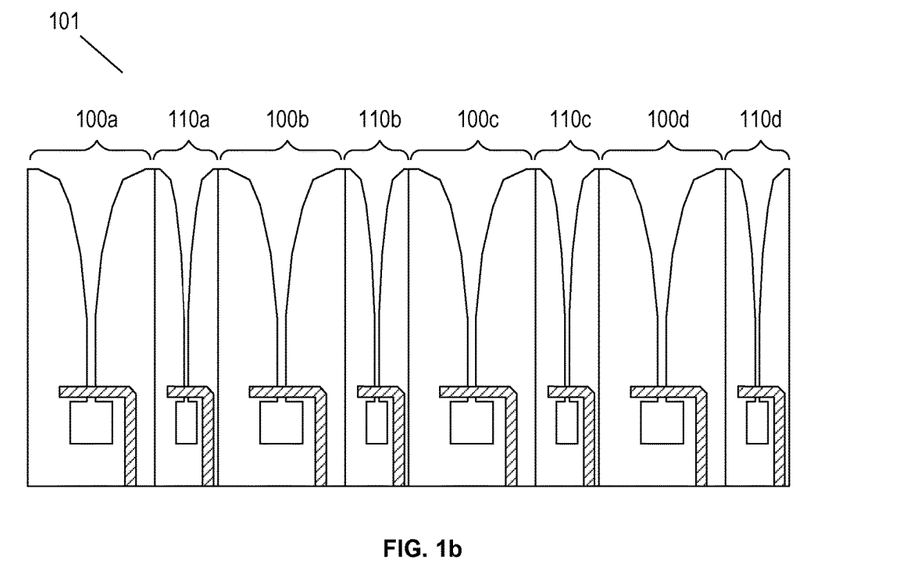
FIG. 1b illustrates a layout of an exemplary one-dimensional heterogeneous antenna array according to an embodiment of the invention.

FIG. 1a illustrates a layout of an exemplary one-dimensional prior-art antenna array 100 having a linear arrangement of congruent "Vivaldi" antenna elements 100a, 100b, 100c, 100d, 100e, and 100f. FIG. 1b illustrates a layout of an antenna array 101 according to an embodiment of the invention. Array 101 includes Vivaldi antenna elements 110a, 110b, 110c, and 110d optimized for higher frequency (or shorter wavelength) interleaved among Vivaldi antenna elements 100a, 100b, 100c, and 100d, which are optimized for lower frequency (or longer wavelength). Vivaldi antenna elements 100a, 100b, 100c, and 100d are congruent with one another, and elements 110a, 110b, 110c, and 110d are likewise congruent with one another. Antenna element 100a and antenna element 110a, however, are transformal with respect to one another, but not congruent, because they differ in at least one physical dimension (in this case, having different widths).

Figure 2:
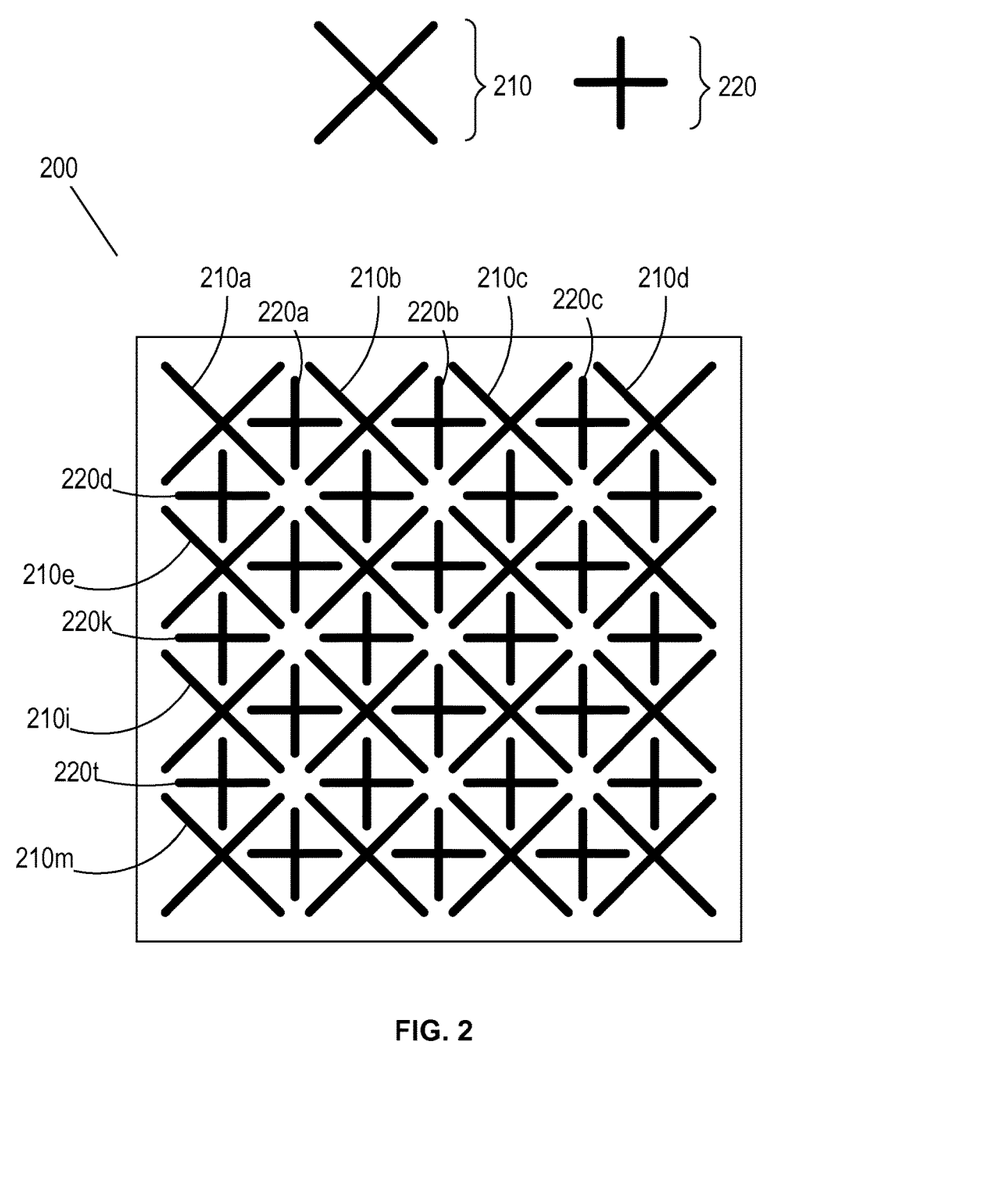
FIG. 2 illustrates a layout of an exemplary two-dimensional heterogeneous antenna array according to another embodiment of the invention.

FIG. 2 illustrates an array 200 according to another embodiment of the invention. Array 200 includes a sub-array of 16 elements based on an element 210, which include antenna elements 210a, 210b, 210c, 210d, 210e, 210i, and 210m; and a sub-array of 24 elements based on an element 220, which include antenna elements 220a, 220b, 220c, 220d, 220k, and 220t. The two sub-arrays are interleaved with one another. It is noted that element 210 and element 220 are transformal, but they are not congruent, because they differ in two physical dimensions (having different lengths and different widths). Element 210 and element 220 are not only designed for different frequencies, but are spatially oriented differently, according to a related embodiment of the invention.

Figure 3:
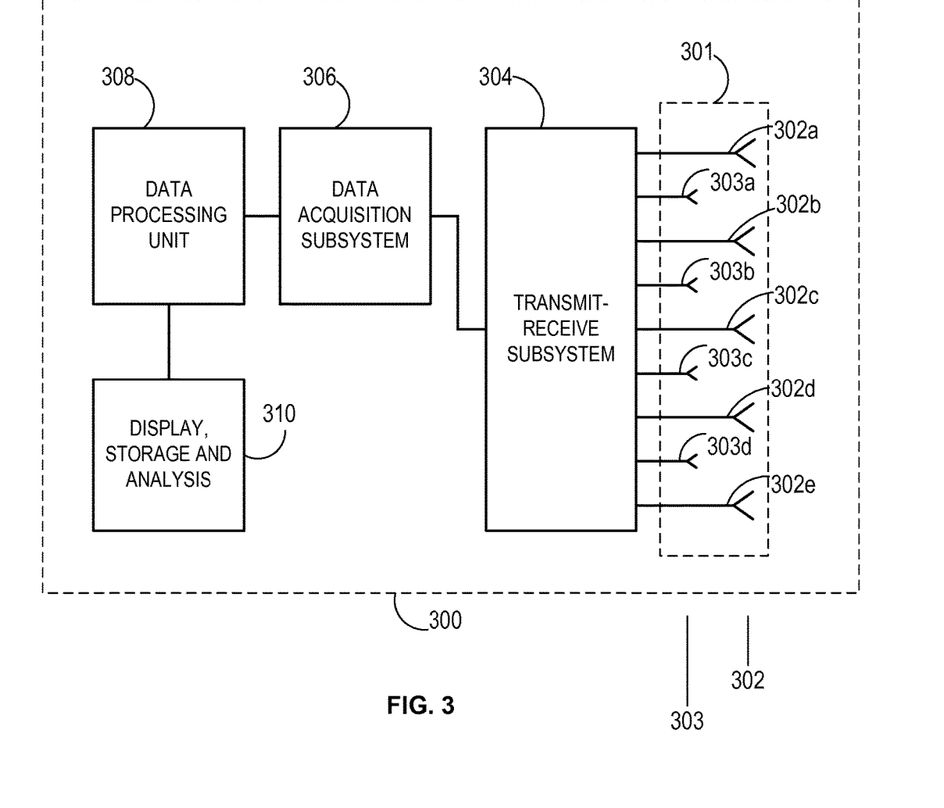
FIG. 3 is a conceptual block diagram of a MIMO-based heterogeneous antenna array microwave imaging system according to an embodiment of the invention.

FIG. 3 is a conceptual block diagram of a MIMO-based heterogeneous antenna array microwave imaging system 300 according to an embodiment of the invention. System 300 includes a heterogeneous antenna array 301 which includes an antenna sub-array 302 and an antenna sub-array 303. Sub-array 302 contains antenna elements 302a, 302b, 302c, 302d, and 302e, which are designed to operate at lower frequencies. Sub-array 303 contains antenna elements 303a, 303b, 303c, and 303d, which are designed to operate at higher frequencies. Antenna array 301 is connected to a transmit-receive subsystem 304, which in turn is connected to a data acquisition subsystem 306, and from thence to a data processing unit 308, which interfaces with the user via a display, storage, and analysis unit 310.

Medical Diagnostic Application

Embodiments of the invention providing high resolution MIMO radar for medical examination and detection of features such as tumors are described below.

These embodiments provide heterogeneous antenna arrays for medical examination, which are configured to be geometrically conformal to the anatomical region being examined. To illustrate these embodiments, the example of examination of human breast tissue for malignancies is presented below, it being understood that the example is non-limiting.

Figure 4:
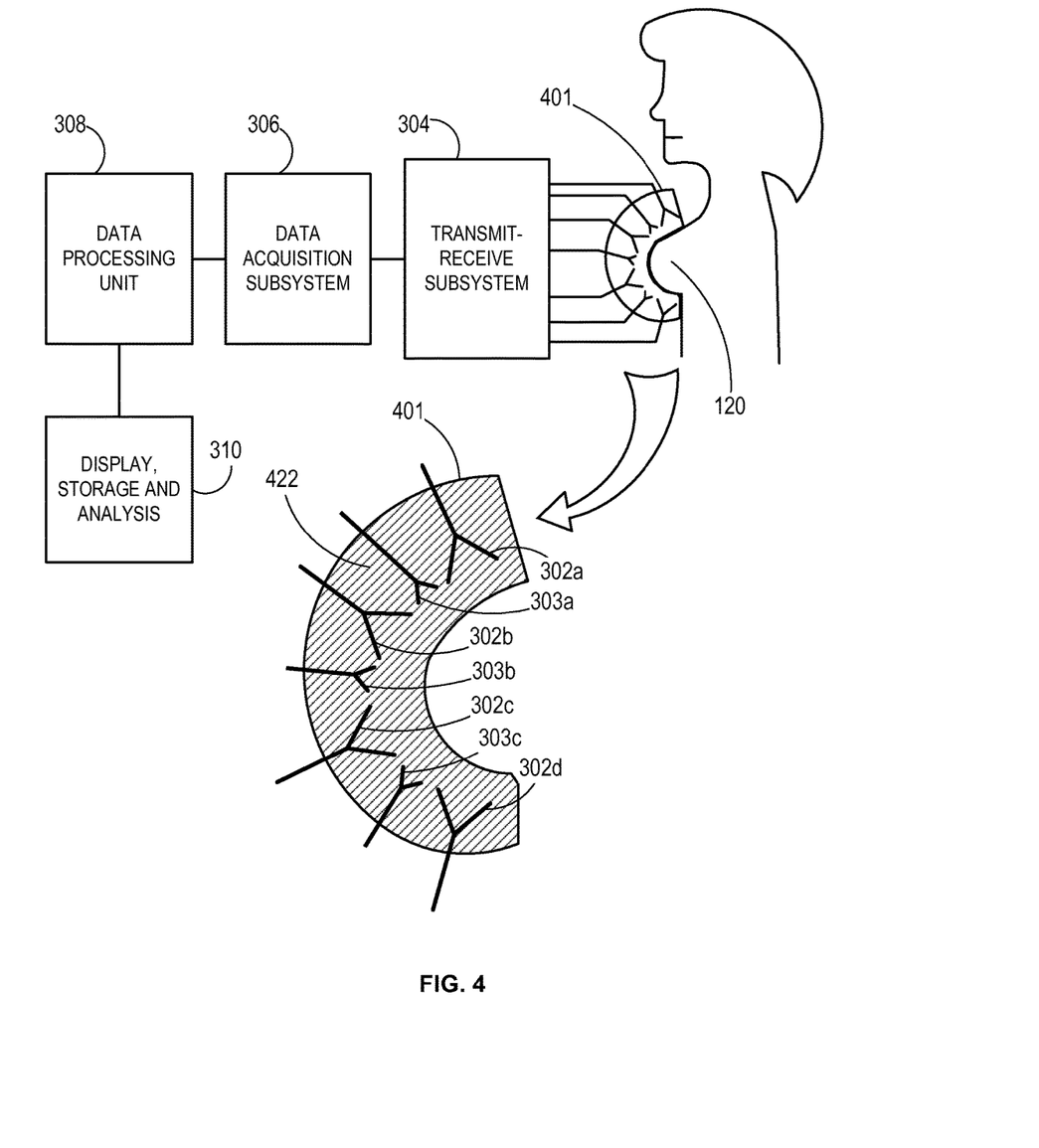
FIG. 4 illustrates a MIMO based microwave heterogeneous antenna array imaging system configuration for breast examination, according to an embodiment of the invention.

FIG. 4 illustrates a MIMO based microwave heterogeneous antenna array imaging system configuration for breast examination and detection of anomalies, such as tumors, according to an embodiment of the invention. A heterogeneous antenna array 401 includes the same elements as array 301 (FIG. 3), but is configured into a non-planar cup-like shape to be geometrically conformal to a patient's breast, with an intermediate matching medium 422 to improve electromagnetic coupling between the antenna element radiation and the breast tissue. In this and related embodiments, the antenna array shape is based on one or more complex surfaces.

Antenna array 401 (FIG. 4) has multiple heterogeneous antenna elements 302a-302d and 303a-303c, typically between a few and a few tens of antenna elements (e.g., 30). The antenna elements can be of types including, but not limited to: printed antenna elements; waveguide antenna elements; dipole antenna elements; and "Vivaldi" broadband antenna elements. In various embodiments of the invention, antenna arrays are in configurations including, but not limited to: linear; two-dimensional; flat; and conformal to the region of interest (e.g., antenna array 401, as illustrated in FIG. 4).

Transmit-receive subsystem 304 is responsible for generating microwave signals, coupling them to antenna elements as described above, receiving reflected microwave signals from antenna elements as described above, and converting them into a form suitable for acquisition. In related embodiments of the invention, signals are of a variety of signal types including, but not limited to: pulse signals; swept-frequency signals; and stepped-frequency signals. Signal-generation circuits utilize components including, but not limited to: oscillators; synthesizers; mixers; and pulse-oriented circuits such as logic gates or step-recovery diodes. Conversion processes include, but are not limited to: down conversion; sampling; and averaging by low-pass filtering, to improve the signal-to-noise ratios and to allow for lower sampling rates. In an embodiment of the invention, transmit-receive subsystem 304 performs transmission and reception with multiple antenna elements at the same time; in another embodiment it may select one transmit and one receive antenna element at a time, according to a tradeoff between complexity and acquisition time.

Data acquisition subsystem 306 collects and digitizes signals from transmit-receive subsystem 304 while tagging the signals according to the antenna element combination used and the time at which the signals were collected. In embodiments of the invention, data acquisition subsystem 304 includes analog-to-digital (A/D) converters and data buffers. In further embodiments, data acquisition subsystem 304 includes additional functions including, but not limited to: signal averaging; correlation of waveforms with templates; and converting signals between frequency and time domain.

Data processing unit 308 converts collected signals into responses characterizing the target object medium under test, and converts the responses into image data. In certain embodiments, data processing unit 308 performs reconstruction methods of other embodiments of the invention. In embodiments of the invention, data processing unit 308 is implemented as a high-performance computing platform, based either on devices including, but not limited to: Digital Signal Processing (DSP) units; general purpose CPUs; and Graphical Processing Units (GPU).

In embodiments of the invention, a final step includes making use of the resulting image, including, but not limited to: visualization; display; storage; archiving; and input to feature detection methods, as handled by display, storage, and analysis console 310. In an embodiment of the invention, console 310 is a general purpose computer with appropriate application software. According to other embodiments, the functional decomposition into processing stages, as illustrated in FIG. 3 and FIG. 4, is implemented on the same hardware (such as a common processing unit); is distributed over multiple processors; and is distributed over remote servers.

In this embodiment, the system operates as follows: The microwave transceiver continually transmits a predesigned signal from one or more of the antenna elements, and receives the signal from one or more other antenna elements. When used for human body visualization, the signals typically occupy frequencies between about 10 MHz and 10 GHz, notably in the 3.1-10.6 GHz range, which allows license-exempt ultra-wideband (UWB) operation at low signal levels. Lower frequencies offer better penetration into the human body, but higher frequencies provide better spatial resolution. Using a wide frequency range allows high temporal resolution, facilitating discrimination of features according to their depth (distance from the antenna elements). There is a variety of choices in selecting signals for microwave imaging applications, such as frequency-swept waveforms and pulse waveforms. According to an embodiment of the invention, making such transmissions allows processing unit 308 to estimate the transfer function of the medium between the transmit antenna elements and receive antenna elements. Processing unit 308 then processes these signals to generate an image.

It is noted that in this application, there are calibration issues related to uncertainty in the physical environment. There may be direct leakage of signal between the antenna elements without passing through the medium under test. Electrical properties of matching medium 422 may vary over time and temperature. The interface between matching medium 422 and target object 120 might generate substantial reflection, depending on the dielectric properties of the object and unknown factors such as inclusion of air bubbles or slight variations in shape.

Image Reconstruction

Certain embodiments of the invention provide methods for reconstructing an image in the frequency domain. According to these embodiments, the received signal includes components which depend on the transfer function between two antenna elements, measured at multiple frequency points, over multiple antenna element pairs, which may span different sub-arrays. To reconstruct the image at a certain point r in space, the received signal is modeled as a contribution of three components:
1) The (unknown) reflection from point r, multiplied by a phasor H representing the phase and amplitude variations (accounting for path loss, antenna element radiation pattern, etc). While the reflection is assumed to be fixed, the phasor H is a function of frequency and antenna element pair. Since different antenna elements in the array are limited to different frequency bands, the phasor H at a certain frequency may be zero for some antenna elements while non-zero for others.
2) The interference caused by reflections from external objects and is the sum over the arena, of similar unknown reflections multiplied by the phasors H. Alternatively this component can be replaced by the interference of an external object at a random location in the arena.
3) White Gaussian noise. The reflections themselves are modeled as unknown parameters with a Gaussian distribution.

Based on the above, an MMSE optimal solution is constructed. However, this solution is not practical due to the numeric complexity and stability issues involved (it requires inverting a matrix whose dimension is the number of measurements, which is potentially large). Therefore, according to specific embodiments of the invention, suboptimal approaches based on per-frequency processing are used.

Figure 5:
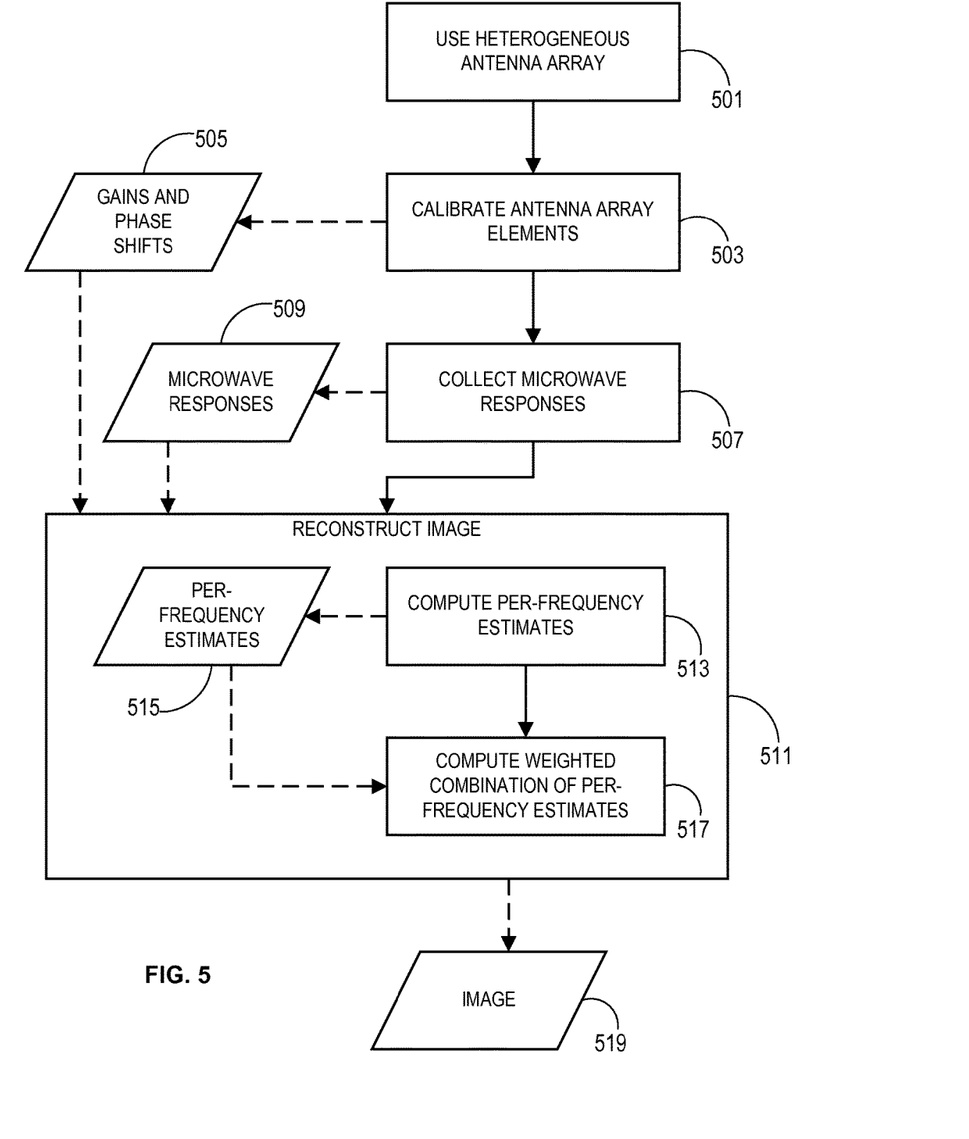
FIG. 5 is a flowchart of an image reconstruction method according to certain embodiments of the invention.

FIG. 5 is a flowchart of a method for enhanced microwave imaging of a region under test, according to an embodiment of the invention.

In a step 501, a heterogeneous antenna array of antenna sub-arrays with different frequency ranges and different densities is used for the region under test;

In a step 503. the antenna elements are calibrated to obtain gains and phase shifts 505 of the antenna elements at different directions and frequencies;

In a step 507 microwave responses 509 are collected for multiple combinations of transmit antenna elements and receive antenna elements, where the transmit and receive antenna elements may belong to the same sub-array or to different sub-arrays; and In a step 511 an image 519 is reconstructed from multiple microwave response signals 509.

In a further embodiment of the invention, reconstruction step 511 for image 519 includes:

A step 513 for computing per-frequency estimates 515 of the properties of the region under test; and A step 517 for computing a weighted combination of per-frequency estimates 515.

According to embodiments of the invention, the image may be reconstructed by the frequency domain methods proposed below. In a related embodiment, a system, such as system 300 (FIG. 3) is configured to perform the above methods.

In certain embodiments of the invention, image reconstruction starts with a collection of responses $h_{ij}(t)$ denoting the impulse response between antenna element i and antenna element j at time t.

The Delay and Sum (DAS) algorithm for reconstructing an image from impulse responses of the medium is well-known, and is used here as a reference. For each point r in some designated volume in the three dimensional space, and for each antenna element pair (from antenna element i to antenna element j) the expected delay $T_{ij}(r)$ from antenna element i to point r and back to antenna element j is calculated, considering the propagation velocity through the medium (which is assumed to have known electrical properties). Then the reconstructed image at location r is created by summing the estimated impulse responses of each pair i,j after shifting them by delay $T_{ij}(r)$, i.e.

$$s(r) = \Sigma_{ij} h_{ij}(T_{ij}(r)) \quad (1)$$

where the summation is over all antenna element pairs.

Assuming a reflector exists at point r then we expect a positive pulse to exist at position Tij(r) in all, or most, pairs, creating high intensity of the reconstructed image at this point.

DAS assumes the responses $h_{ij}(t)$ refer to the impulse response of the medium under test. However since the components involved in the measurement have responses varying in frequency and space, the direct measurement involves a combination of the medium response and the response of these components. The antenna elements used for transmission and reception proposes are usually of a high-pass nature, not being capable of transmitting very low frequencies. The frequency response of transmission/receive microwave circuits may exhibit variations due to production, aging, and temperature, and it is preferable to measure that response and take it into account.

Typical image reconstruction algorithms (such as DAS) assume perfect antenna elements, and therefore the above effects are compensated for before applying the reconstruction algorithm, e.g. by dividing the frequency response obtained from the measurement by the known frequency response of the components. As mentioned previously, this pre-calibration compensation is sub-optimal as it amplifies noise, and does not take into account that some antenna elements at some frequencies see a target better than others, nor does it apply to location-dependent amplitude and phase shift variations.

The alternative algorithms described below are based on the following frequency domain model for the received signal:

$$Y_{ij}(f) = \sum_r H_{ij}^{(r)}(f) \cdot s(r) + v_{ij}(f) = \underbrace{H_{ij}^{(r)}(f) \cdot s(r)}_{Signal} + \underbrace{\sum_{r' \neq r} H_{ij}^{(r')}(f) \cdot s(r')}_{Interference} + \underbrace{v_{ij}(f)}_{Noise} \quad (2)$$

where:

$Y_{ij}(f)$ is an estimated transfer function from transmitter to receiver measured from antenna element i to antenna element j, at frequency f. The relevant antenna element pairs contain all antenna element pairs for which a measurement of the transfer function was made (and they may be from the same sub-array, or from different sub-arrays). In a frequency domain measurement method, the sample $Y_{ij}(f)$ is obtained directly by measuring the system response to a sine wave at frequency f.

r is the location in space (represented, e.g. by a 3 dimensional vector).

s(r) is the reflectivity of the object at location r. The image that will be reconstructed consists of an estimate of s(r) for all r-s in the arena (the region in space the image represents). The variable s(r) is modeled as a zero mean unit variance Gaussian random variable, independent with respect to different points.

$H_{ij}^{(r)}(f)$ is a transfer function representing all known gain and phase variations that the signal experiences in the transmit and receive path to and from the designated location r. The most important component of $H_{ij}^{(r)}(f)$ is simply $e^{-j2\pi f T_{ij}^{(f)}(r)}$ which models the phase contribution of the propagation delay $T_{ij}^{(f)}(r)$, but note that here we can allow this delay to be frequency dependent (e.g. due to the frequency dependence of $\in_r$). $H_{ij}^{(r)}(f)$ further includes the response of electrical components, cables, the antenna element frequency dependent radiation pattern, path loss, etc. In cases where the transfer function of certain antenna element pairs was not measured at certain frequencies, as would occur in a heterogeneous array, $H_{ij}^{(r)}(f)$ is simply set to 0 for those antenna element pairs and frequencies.

$v_{ij}(f)$ is the thermal and measurement noise which is modeled as a complex Gaussian noise with variance $\sigma^2$, independent with respect to frequency points and antenna element pairs.

In the signal model in Equation (1) there are three components. The first ("Signal") accounts for the desired signal arriving from the point of interest r. The second ("Interference") accounts for signals arriving from other points in space (the summation over r' should include all points in the arena, and possibly points outside the arena which can produce significant interference). The last component is the noise. The inclusion of the interference component is an important step, since without it, an MMSE estimate reconstruction algorithm would attempt to maximize the "Signal to noise" ratio at each point. The result would be optimal in terms of minimizing the effect of the thermal noise, but would not take into account the interference caused by other reflectors and these reflectors (at point r') may have a significant impact on the estimate at point r, and thus each object would smear in the reconstructed image. The interference component cannot be treated as noise since unlike noise, it is highly correlated between antenna element pairs, and this correlation can be used to improve the image.

The MMSE solution to this problem is highly complex. In order to compute it requires calculating the covariance matrix of the measurements. The dimension of this matrix is the number of antenna element pairs times number of frequency points. For example if there are 30 antenna elements (435 pairs) and the frequency range is 50 Mhz to 10 Ghz in steps of 50 Mhz (200 points), then the dimension is 435*200=87000, i.e. the matrix would be 87000×87000. Therefore this solution is practical only when the number of measurements is relatively small. The elements of this matrix are indexed by the triple (i,j,f) in each of its two axes and are:

$$C_{YY}(i_1 j_1 f_1, i_2 j_2 f_2) = E[Y_{i_1 j_1}(f_1) \cdot Y_{i_2 j_2}(f_2)^*] = \sum_r H_{i_1 j_1}^{(r)}(f_1) H_{i_2 j_2}^{(r)}(f_2) + \sigma^2 \cdot \delta_{(i_1 j_1 f_1) = (i_2 j_2 f_2)} \quad (3)$$

where $\delta_{(i_1 j_1 f_1) = (i_2 j_2 f_2)}$ is 1 if $(i_1, j_1, f_1) = (i_2, j_2, f_2)$ and zero otherwise. The MMSE solution for point r is $$\hat{s}(r) = Re\{\underline{h}(r)^* C_{YY}^{-1} \underline{y}\} \quad (4)$$

where $\underline{h}(r)$ is a vector collecting all $H_{ij}^{(r)}(f)$ (for all triples i,j,f), and $\underline{y}$ is a vector collecting all $Y_{ij}(f)$ in the same order.

Due to the high complexity of calculating the MMSE solution when the number of measurements is large, suboptimal solutions are used. One suboptimal embodiment of the invention accounts only for the total noise in each frequency and antenna element pair. Define $\sigma_{ij}^2(f)$ as the total noise and interference power in pair i,j at frequency f, which equals $$\sigma_{ij}^2(f) = \sigma^2 + \sum_r |H_{ij}^{(r)}(f)|^2.$$

Modeling $Y_{ij}(f)$ as $H_{ij}^{(r)}(f) \cdot s(r)$ plus an independent noise term with power $\sigma_{ij}^2(f)$, resulting in the following simple combiner which is obtained as the MMSE solution:

$$\hat{s}_1(r) = \text{Re}\left\{\frac{\sum_{ij}\sum_f \frac{1}{\sigma_{ij}^2(f)} H_{ij}^{(r)}(f)^* Y_{ij}(f)}{1 + \sum_{ij}\sum_f \frac{1}{\sigma_{ij}^2(f)} |H_{ij}^{(r)}(f)|^2}\right\} \quad (5)$$

While this simple combiner does not take into account the correlation in the interference between different frequencies and antenna element pairs, it does take into account the noise power. Note that if one of the antenna elements has low gain, it would usually affect both the numerator and the denominator so the signals would be scaled back. However if it has a low gain in one direction and a high gain in another, the directions in which it has low gain would be scaled down, because $H_{ij}^{(r)}(f)$ is small for these directions, while the $\sigma_{ij}^2(f)$ that accounts for interference from all directions, is high. Note that if one assumes the simple model where H consists of path delay only $H_{ij}^{(r)}(f) = e^{-j2\pi f T_{ij}(r)}$ and assumes $\sigma_{ij}^2(f)$ is constant, then the numerator becomes a summation of the time domain signals (since the summation over f yields an inverse DFT), and denominator is constant, and thus we obtain the DAS algorithm as a special case.

In another low complexity embodiment of the invention de-correlation is applied per frequency. In this solution one first generates an estimate from the measurements of all antenna element pairs in a each frequency separately, and then combines these estimates. The per-frequency estimator performs the same operations as described for the MMSE solution (Equations (4), (5)) except the frequency index is fixed $f_1 = f_2 = f$ and therefore the dimension of $C_{YY}$ equals the number of pairs. The resulting per-frequency estimators are combined while scaling them according to their variance. The advantage of this solution over the previous one described is in its ability to utilize the correlation of the interference between antenna element pairs to reduce the effect of this interference and produce a cleaner image.

In another embodiment of the invention, a more elaborate model of the received signals is used, which includes frequency-dependent reflectivity. Different materials, and particularly different human tissues, may be separated not only based on their reflectivity but also based on the frequency dependence of their reflectivity. The model in Equation (2) may be replaced by $$Y_{ij}(f) = \sum_r H_{ij}^{(r)}(f) \cdot s(r) \cdot g_{\theta(r)}(f) + v_{ij}(f),$$

where $\theta(r)$ describes the frequency dependent behavior in a point in space, and $g_\theta(f)$ defines the frequency domain gain resulting from this equation. In a particular case, $g_{74}(f)$ may be a linear function describing a linear dependence in frequency $g_\theta(f) = 1 + \theta \cdot f$. Using this model, the MMSE equations for deriving $s(r)$ and $\theta(r)$ from the measurements are derived for the various embodiments described above. For brevity, this can be done using the same set of equations as above, while treating $\theta(r)$ as if it was another set of points in the arena, with a transfer function $H_{ij}^{(r)}(f)' = f \cdot H_{ij}^{(r)}(f)$.

It will be readily understood by those skilled in this art that there are many variation possible without deviating from the scope and spirit of present invention. In particular, the variations may include application to different body parts in humans, or to other objects. Different response collection sequences can be used, as well as different signals can be used for probing the medium under test. The present invention can be used in conjunction with different methods of reconstructing the images from response measurements. The reconstruction algorithms were described by frequency domain representation for simplicity, but may be implemented in other forms of signal representation (for example time domain, or performed directly from the measurements of the signals at the receiver). The reconstruction algorithms described are based on the signal and interference model and are all simplifications of the MMSE solution, and other simplifications are possible as well. Furthermore, the frequency domain reconstruction algorithm described above may be used separately from the heterogeneous array, and vice versa.

Algorithms according to various embodiments of the invention are based on MMSE estimation of $s(r)$ from all measurements $Y_{ij}(f)$ (over all frequencies and antenna element pairs).

A further embodiment of the invention provides a computer product including a computer-readable non-transient tangible storage medium containing executable instructions for a computer to perform methods disclosed herein, or variations thereof.

As described hereinabove, the antenna array apparatus of the present invention may be used to detect a pathological disorder, which in one embodiment, is a cancer and in another embodiment, a tumor. In another embodiment, the antenna array apparatus of the present invention may used to treat a pathological disorder, which in one embodiment, is a cancer and in another embodiment, a tumor. In one embodiment, the antenna array apparatus of the present invention is used in hyperthermia therapy. In one embodiment, hyperthermia therapy uses microwaves to destroy or inactivate cells and/or tumors with heat. In one embodiment, the cells are cancer cells. In one embodiment, hyperthermia therapy using the antenna array apparatus of the present invention may be used in combination with radiotherapy and/or chemotherapy for improved efficacy. Clinical studies have shown that treatment with conventional radiotherapy and chemotherapy in combination with hyperthermia may double the long-term ability to cure certain forms of cancer, such as cervical cancer and soft-tissue sarcoma.

In another embodiment, the antenna array apparatus of the present invention may be used for theranostics, which in one embodiment, is a combination of diagnosis and treatment.

In one embodiment, the cancer detected and/or treated using the antenna array apparatus of the present invention is carcinoma, sarcoma, lymphoma, blastoma, glioblastoma, or melanoma. In one embodiment, the tumor detected and/or treated using the antenna array apparatus of the present invention is a brain, esophygeal, nasal, buccal, throat, lymphatic, lung, breast, bone, liver, kidney, prostate, cervical, head and neck, skin, stomach, intestinal, or pancreatic tumor, or a combination thereof. In one embodiment, the antenna array apparatus of the present invention is used to detect or treat breast cancer. In another embodiment, the antenna array apparatus of the present invention is used to detect or treat prostate cancer.

In one embodiment, the antenna array apparatus of the present invention is used to detect or treat a precancerous condition. In one embodiment, the precancerous condition is benign prostatic hyperplasia (BPH), actinic keratosis, Barrett's esophagus, atrophic gastritis, cervical dysplasia, or a precancerous breast lesion.

In one embodiment, the shape of the apparatus is adjusted to conform with the shape of the body at the point at which the apparatus is attached, as shown in FIG. 4 for breast, and as would be clear to a skilled artisan. In one embodiment, the configuration of the apparatus is adjusted to conform with the shape of the body at the point at which the apparatus is attached, as would be clear to a skilled artisan. In one embodiment, the apparatus further comprises an apparatus for securing tissue in a fixed position and to prevent tissue from moving during diagnosis, treatment, or a combination thereof.

In one embodiment, the present invention provides a method of detecting, treating, or both detecting and treating a pathological disorder in a tissue of a subject comprising the step of contacting said subject with a heterogenous wideband antenna array as described herein, and a microwave source and, optionally, a processor connected to the receiver for processing the amplitude and phase information to detect and locate said cancer in said tissue of said subject.

In one embodiment, the present invention provides a method of detecting, treating, or both detecting and treating cancer or a tumor in a tissue of a subject comprising the step of contacting said subject with a heterogenous wideband antenna array as described herein, wherein the array further comprises a microwave receiver, which in one embodiment, has amplitude and phase shift detectors for receiving reflected microwave signals and, optionally, a processor connected to the receiver for processing the amplitude and phase information to detect and locate said cancer in said tissue of said subject. As is known in the art, cancerous tissue has different water content and/or electric properties which allows microwaves to be used in diagnostics of cancer, in one embodiment cancer of the breast.

What is claimed is:

1. A radar system for reconstructing an image by computing a weighted combination of per-frequency estimates, the radar system comprising:
   a heterogeneous wideband antenna array apparatus; and
   a data processing unit connected to the heterogeneous wideband antenna array apparatus;
   wherein the heterogeneous wideband antenna array apparatus includes:
   a first sub-array comprising one or more antenna elements congruent to a first antenna element which is optimized to operate within a first frequency range; and
   a second sub-array comprising one or more antenna elements congruent to a second antenna element which is optimized to operate within a second frequency range;
   and wherein:
     the first frequency range is different from the second frequency range;
     the first frequency range and the second frequency range overlap;
     the first antenna element is not congruent to the second antenna element;
     antenna elements of the first sub-array and antenna elements of the second sub-array are interleaved such that at least one antenna element of the antenna array apparatus is surrounded by antenna elements which are not congruent to the at least one antenna element;
   and wherein:
   the data processing unit is operative to:
   collect a plurality of microwave responses for a plurality of combinations of transmit antenna elements and receive antenna elements of the antenna array apparatus, respectively, wherein each combination includes a transmit antenna element and a receive antenna element;
   compute a plurality of per-frequency estimates of a frequency-domain transfer function based on the plurality of microwave responses for the plurality of combinations of transmit antenna elements and receive antenna elements of the antenna array apparatus, wherein each per-frequency estimate is based on a measurement using a transmit antenna element and a receive antenna element of the heterogeneous wideband antenna array apparatus at a specified frequency;
   compute a plurality of estimated reflectivities at a plurality of three-dimensional locations, wherein each estimated reflectivity is computed based on a combination of the per-frequency estimates of the frequency-domain transfer function weighted by a phasor, wherein the phasor is a function of the transmit antenna element and the receive antenna element at the specified frequency; and
   reconstruct an image according to a function of the plurality of estimated reflectivities.

2. The radar system of claim 1, wherein the first antenna element is transformal in at least one physical dimension with respect to the second antenna element, without being congruent thereto.

3. The radar system of claim 1, wherein antenna elements of the first sub-array and antenna elements of the second sub-array are interleaved such that at least one antenna element of the first antenna sub-array is surrounded by antenna elements of the second sub-array, and at least one antenna element of the second sub-array is surrounded by antenna elements of the first sub-array.

4. The radar system of claim 1, wherein a density of antenna elements covering the first frequency range is different from a density of antenna elements covering the second frequency range.

5. The radar system of claim 4, wherein one of (i) the density of antenna elements operating within the first frequency range, or (ii) the density of antenna elements operating within the second frequency range is a function of the combined densities of both the antenna elements of the first sub-array and the antenna elements of the second sub-array.

6. The radar system of claim 1, wherein the heterogeneous wideband antenna array apparatus is optimized for near-field microwave imaging.

7. The radar system of claim 1, wherein the heterogeneous wideband antenna array apparatus is configured to be geometrically conformal to an anatomical region for examination.

8. The radar system of claim 7, wherein the anatomical region for examination is a human breast.

* * * * *